(12) United States Patent
Daugherty et al.

(10) Patent No.: US 10,226,429 B2
(45) Date of Patent: Mar. 12, 2019

(54) ENTERIC COATED, SOLUBLE CREATINE AND POLYETHYLENE GLYCOL COMPOSITION FOR ENHANCED SKELETAL UPTAKE OF ORAL CREATINE

(75) Inventors: F. Joseph Daugherty, Omaha, NE (US); John R. Palmer, Jr., Barrington Hills, IL (US); Michael S. Tempesta, El Granada, CA (US)

(73) Assignee: CRYXA LLC, Omaha, NE (US)

( * ) Notice: Subject to any disclaimer, the term of this patent is extended or adjusted under 35 U.S.C. 154(b) by 0 days.

(21) Appl. No.: 12/763,901

(22) Filed: Apr. 20, 2010

(65) Prior Publication Data

US 2010/0203090 A1  Aug. 12, 2010

Related U.S. Application Data

(62) Division of application No. 12/133,328, filed on Jun. 4, 2008, now abandoned.

(60) Provisional application No. 60/942,176, filed on Jun. 5, 2007.

(51) Int. Cl.
*A61K 31/198* (2006.01)
*A61K 9/28* (2006.01)
*A61K 9/16* (2006.01)

(52) U.S. Cl.
CPC ............ *A61K 9/2866* (2013.01); *A61K 9/282* (2013.01); *A61K 9/286* (2013.01); *A61K 31/198* (2013.01); *A61K 9/1641* (2013.01)

(58) Field of Classification Search
CPC ............................ A61K 31/197; A61K 31/198
See application file for complete search history.

(56) References Cited

U.S. PATENT DOCUMENTS

| | | | |
|---|---|---|---|
| 5,773,473 A * | 6/1998 | Green et al. ................. 514/565 |
| 6,399,661 B1 | 6/2002 | Golini | |
| 6,897,334 B2 | 5/2005 | Vennerstrom | |
| 7,608,641 B2 | 10/2009 | Miller et al. | |
| 2003/0078517 A1 | 4/2003 | Kensey | |
| 2004/0001802 A1 | 1/2004 | Mayumi et al. | |
| 2004/0013732 A1 * | 1/2004 | Farber et al. ................. 424/488 |
| 2005/0226840 A1 | 10/2005 | Kaddurah-Daouk | |
| 2006/0062849 A1 | 3/2006 | Byrd | |
| 2006/0062853 A1 | 3/2006 | Byrd | |
| 2006/0194877 A1 | 8/2006 | Gardiner et al. | |
| 2007/0065511 A1 | 3/2007 | Tallon et al. | |
| 2007/0071815 A1 | 3/2007 | Byrd | |
| 2009/0253797 A1 | 10/2009 | Miller et al. | |
| 2011/0034421 A1 | 2/2011 | Miller et al. | |

OTHER PUBLICATIONS

Jenner. "Presymptomatic Detection of Parkinson's Disease." J Neural Transm Suppl. 1993; 40:23-36 (Abstract Only).*
"Carbowax Pharmaceuticals Polyehtylene Glycols", 1998, Union Carbide Corporation Industry Guide Series, Danbury, CT, US, pp. 1-2.
"Carbowax Sentry—Polyethylene Glycols and Methoxypolyethylene Glycols for Pharmaceuticals", The Dow Chemical Company, 1995-2007, www.dow.com/polyglycols/carbowax, pp. 1-4.
PCT/US08/65805, PCT International Search Report, dated Sep. 2, 2008, pp. 1-2.
M. Spillane, et al., "The effects of creatine ethyl ester supplementation combined with heavy resistance training on body composition, musle performance, and serum and muscle creatine levels", J. of the Internat'l Soc. of Sprots Nutrition, publ. Feb. 19, 2009, 6:6, p. 1-14.
Label for C2 Strength 100% Creatine Ethyl Ester HCI capsules, (c) 2009, Labrada Nutrition, Houston, TX.
The Dow Chemical Company, A Guide to Glycols, (c) 2003, pp. 1-10.
The Dow Chemical Company, DOW(TM) Propylene Glycol, revised Oct 3, 2013, pp. 1-6.
Sigma-Aldrich , Solubility Information, http://www.sigmaaldrich.com/united-kingdom/technical-services/solubility.printerview.html, pp. 1-2, printed Jun. 23, 2016.
Celly, Celly Creatine HCL, http://celly creatine.com/science/solubility, pp. 1-3, printed Jun. 23, 2016.
https://en.wikipedia.org/wiki/Plyethylene_glycol (2018).

* cited by examiner

*Primary Examiner* — Leslie A. Royds Draper

(57) ABSTRACT

An oral creatine formulation includes soluble creatine and polyethylene glycol, coated with an enteric coating. The most preferred soluble creatine is creatine HCl. The most preferred polyethylene glycols have an average molecular weight of from 3150 to 3685, although for particular formulation formulations and particular uses, the average molecular weight polyethylene glycols may range from 190 to 9000.

8 Claims, 3 Drawing Sheets

US 10,226,429 B2

ENTERIC COATED, SOLUBLE CREATINE AND POLYETHYLENE GLYCOL COMPOSITION FOR ENHANCED SKELETAL UPTAKE OF ORAL CREATINE

RELATED APPLICATION

The present application is a divisional filing of U.S. patent application Ser. No. 12/133,228 filed Jun. 4, 2008, which claims priority of U.S. Provisional Application No. 60/942,176 filed Jun. 5, 2007, both of which applications are incorporated herein in their entireties by this reference.

FIELD OF THE INVENTION

The present invention relates to creatine formulations adapted for use as source of dietary creatine, and methods of use thereof.

BACKGROUND OF THE INVENTION

It is known that dietary ingestion of creatine monohydrate is preferentially taken up by skeletal muscle. Indeed, creatine is used heavily as a dietary supplement for performance enhancement by athletes. This is because the creatine, once present muscle tissue where it is stored as creatine phosphate, reacts with adenosine diphosphate (ADP) to restore adenosine triphosphate (ATP) levels and provide energy needed for muscle activity. By ingesting creatine, athletes are able to load their muscle tissue with higher levels of creatine phosphate and are able to better sustain muscle activity.

Although many forms of creatine are stable ex vivo, including the creatine monohydrate and numerous esters, creatine and creatine monohydrate are known to be typically unstable in vivo, i.e., in the acidic environment that exists in the stomach, and the basic conditions of the lower gastrointestinal tract. So, for example, it is known that creatine monohydrate, which is a commonly ingested form of creatine, rapidly breaks down in the stomach to form creatinine. Furthermore, because creatine monohydrate is not easily fully solubilized in cold or room temperature water, it is often dissolved in fruit juices and other acidic liquids, which also promote degradation of creatine to creatinine and excretion. For these reasons, other forms of creatine, particularly creatine ethyl esters, have been the focus of product development. However, such compounds also suffer from solubility and degradation problems.

In an effort to create a stable form of creatine in which the creatine would be better protected from degradation while present in the stomach and intestines, tests were conducted in which polyethylene glycols were reacted with creatine in the presence of acid catalysts, including $H_2SO_4$, HCl and $H_3PO_4$. Although the temperature was varied from 20° C. to 100° C. using a wide variety of organic and mineral acid catalysts, the polyethylene creatine esters did not form in substantial quantities and/or degraded rapidly, to creatinine. Moreover, the resulting creatine polyethylene esters did not exhibit a desired level of stability in low pH environments of the reaction mixture, analytical test methods or in stomach equivalent acidic environments.

Thereafter, the starting creatine component was first substituted with creatine monohydrate and thereafter with creatine HCl, with no improvement in production results.

To avoid degradation a different route was then chosen to produce an acceptable polyethylene glycol ester. Instead of using creatine as a starting material, creatine ethyl ester and creatine ethyl ester HCl were used as starting materials and reacted with polyethylene glycol under acid and alkaline conditions to trans-esterify the ethyl ester to creatine polyethylene glycol ester and ethanol. This approach yielded similar results in that the yield of creatine polyethylene glycol esters were again low and degraded rapidly to creatinine.

High-performance liquid chromatography (HPLC) test methods were used to test purities of the various starting materials and the desired polyethylene glycol ester. These test methods clearly showed the degradation of the creatine compounds to creatinine. In particular the ester compounds degraded faster than the starting materials of creatine, creatine monohydrate and creatine HCl. The test methods themselves also caused the creatine compounds to degrade as well during the test. Thin layer chromatography (TLC) was used with both alkaline and acidic mobile phases and showed similar results.

Other commercially available creatine esters, such as creatine ethyl ester and creatine ethyl ester HCl, were also tested for stability in low pH environments. Surprisingly, the ethyl esters, thought to be able to resist degradation better, were found to also degrade rapidly to creatinine, as did creatine, creatine monohydrate and creatine HCl.

The solubility and degradation problems associated with creatine typically result in low absorbance of ingested creatine. When absorbance is low, high doses must be taken to achieve desired levels in the blood and muscles. To accomplish this, a regimen of a creatine supplement of 20-30 grams per day is typically taken to compensate for the substantial loss of the creatine to degradation when dissolution and/or degraded by digestion into creatinine. Unfortunately, the presence of substantial amounts of creatinine in the digestive tract can cause digestive problems such as severe cramping, due to the toxic nature of creatinine.

Accordingly, development of a creatine formulation in which the creatine is in a form which is resistant to rapid degradation to creatinine, i.e., stable in acid and base environments of the stomach and gut, but which is ultimately absorbed with enhanced efficacy by skeletal muscle, remains needed.

SUMMARY OF THE INVENTION

A most preferred embodiment of a creatine formulation of the present invention includes creatine hydrochloride (herein creatine.HCl) and polyethylene glycol (PEG), coated with an enteric coating. While the average molecular weight of the PEG component can vary, and indeed, there may be substantial variation in the range of PEG chain length, a preferred range of the average molecular weight of a PEG component suitable for human consumption is from 150 to 9000. A more preferable range of average molecular weight of the PEG component is from 3015 to 4800. The most preferred PEGs have an average molecular weight of from 3150 to 3685.

Preferred ratios by weight percent of creatine equivalents to PEG are from 99:1 to 50:50. A more preferred range is from 95:5 to 90:10.

A preferred daily dosage of the creatine equivalent of the creatine formulation is from 0.1 to 10 grams per day. Alternate dosages to be suitable for maintenance dosages to maintain previous creatine loading regimens, are from 0.5 to 2 grams per day of the creatine equivalent component of the formulation. Even lower dosages of from 0.01 to 0.5 grams per day of the creatine equivalent of the formulation are expected to have beneficial results, especially for older people. Therapeutic does for muscle-wasting diseases or conditions or for those undergoing musculoskeletal stress could exceed these levels and be has high as 10-20 grams per day.

It is contemplated that other soluble creatine, i.e., forms of creatine being more soluble than creatine monohydrate (creatine.$H_2O$) in room temperature aqueous solutions, may be combined with PEG to form a blend or dispersion to be coated with an enteric coating.

It is further contemplated that the creatine formulations of the present invention may be useful for minimizing symptoms of Parkinson's disease and of muscle-wasting diseases. Higher dosages, for example, from 2 to 20 grams per day, are recommended to minimize symptoms of Parkinson's disease and muscle wasting diseases and conditions

BRIEF DESCRIPTION OF THE DRAWINGS

The accompanying drawings, which are incorporated herein and form a part of the specification, illustrate non-limiting embodiments of the present invention, and together with the description, serve to explain the principles of the invention.

DETAILED DESCRIPTION OF PREFERRED EMBODIMENTS

Figure 1:
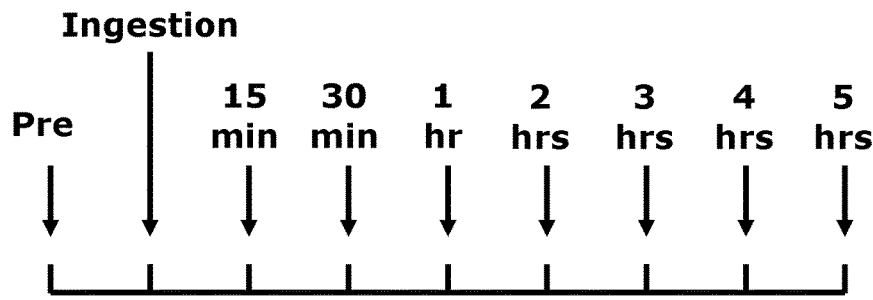
FIG. 1 graphically illustrates a time line for sampling blood relative to ingestion of a formulation of the present invention and a control supplement in an experimental study described herein.

A creatine formulation of the present invention includes a soluble creatine and polyethylene glycol (PEG), coated with an enteric coating. The most preferred form of the PEG component contains an average molecular weight of 3015 to 3685 and is marketed under the Carbowax® PEG 3350 trade name, which at ambient temperature, is a hard, opaque white, granular solid. The most preferred form of the soluble creatine is the creatine.HCl salt, which at room temperature, is preferably obtained in powdered or crystalline form. The most preferred formulation of the present invention, is a solid dispersion of the creatine.HCl salt in the PEG 3350, with the dispersion then coated with an enteric coating. However, other forms of creatine acceptable for use in the formulations of the present invention are soluble creatine, defined here as those creatine salts of food grade quality which are more soluble in room temperature aqueous solutions than creatine monohydrate (creatine.$H_2O$).

Other preferred PEGs are opaque granular solids, including PEG having an average molecular weight of from 1305 to 1595 (e.g., Carbowax® PEG 1450), of from 3600 to 4400 (e.g., Carbowax® PEG 4000), of from 4400 to 4800 (e.g., Carbowax® PEG 4600), and of from 7000 to 9000 (e.g., Carbowax® PEG 8000). PEG having an average molecular weight of from 6000 to 7500 (e.g., Carbowax® PEG 6000) is also preferred.

A preferred daily dosage of the creatine formulation for creatine loading contains from 0.1 to 10 grams per day of creatine equivalent in a formulation of the present invention. In the most preferred embodiment, this means that from 0.1 to 10 grams per day of creatine equivalent in the form of creatine HCl is ingested. Alternate dosages, which may be suitable for maintenance dosages to maintain previous creatine loading regimens, are from 0.5 to 2 grams per day of creatine equivalents in a formulation of the present invention. Even lower dosages of from 0.01 to 0.5 grams per day of creatine equivalent in a formulation of the present invention are expected to have beneficial results, and may be particularly suitable for oral supplements for the elderly. Conversely, higher doses of 10-20 grams per day of creatine equivalent in a formulation of the present invention are also contemplated.

To compare the uptake efficacy of a conventional creatine.$H_2O$ supplement with the soluble creatine most preferred herein, which is a creatine.HCl/PEG composition coated with an enteric coating, a test was conducted with 17 healthy male study participants. The participants selected had the following characteristics:

| | |
|---|---|
| Age | 23.5 years ± 1.0 year |
| Height | 176.1 centimeter (cm) ± 2.2 cm |
| Weight | 84.8 kilogram (kg) ± 4.0 kg |
| Fat percent (by weight) | 17.4% ± 2.5% |

Study participants were randomly divided into a control group of 9 and an experimental group of 8. Resting, fasted blood samples were taken pre- and post-supplementation period to monitor health-related variables. Muscle biopsies were also taken pre- and post-supplementation period.

The control group ingested 20 grams per day (gm/day) of creatine.$H_2O$ for a supplementation period of 5 days. The experimental group ingested 10 gm/day of creatine equivalent for 5 days in the form of creatine HCl/PEG formulated in weight percents of approximately 93% creatine HCl to 7% PEG, coated with an enteric coating comprising cellulose, sodium alginate, medium chain triglycerides and oleic and stearic acid, and then formed into tablets. Gastrointestinal absorption of creatine to the circulation over the five hour period following ingestion was determined via indwelling catheters on the first day of supplementation. The pre- and post-supplementation period muscle biopsies were used to determine relative myosin heavy chain (MHC) content, cellular adenosine triphosphate ("ATP"), creatine phosphate, free creatine, and total creatine concentrations.

TABLE 1

| | CONTROL creatine•$H_2O$ | | EXPERIMENTAL creatine HCl/PEG | |
|---|---|---|---|---|
| | pre-suppl. | post-suppl. | pre-suppl. | post-suppl. |
| CELLULAR ATP (molar ratio) | 4.48 ± 0.30 | 5.07 ± 0.24 | 4.39 ± 0.15 | 4.88 ± 0.13 |
| free creatine $\mu M \cdot g_{dw}^{-1}$ | 23.0 ± 4.2 | 39.2 ± 2.7 | 22.1 ± 2.9 | 33.6 ± 3.2 |

TABLE 1-continued

| | CONTROL creatine•H$_2$O | | EXPERIMENTAL creatine HCl/PEG | |
|---|---|---|---|---|
| | pre-suppl. | post-suppl. | pre-suppl. | post-suppl. |
| total creatine µM·g$_{dw}{}^{-1}$ | 94.7 ± 5.4 | 114.8 ± 7.4 | 92.6 ± 5.4 | 106.6 ± 8.4 |
| UPTAKE EFFICACY | | 5.85 ± 1.85 | | 9.86 ± 2.21 |

Both the control and experimental groups exhibited significantly elevated concentrations of both free creatine and total creatine by the end of the study. These differences were also apparent when the values were adjusted for ATP (molar ratio).

Although not different statistically, creatine uptake efficiency was considerably greater for creatine HCl/PEG as compared to creatine.H$_2$O, as indicated by a moderately-large effect size calculated as $$\frac{(\text{total creatine})/(\text{cellular } ATP)}{(\text{total grams ingested creatine})}$$

Noticeably, circulatory uptake of creatine was significantly different between the control and experimental groups, with blood concentrations (milligrams per liter per day—mg g dL$^1$) for the control group peaking at two hours post-ingestion (25.99±2.96 mg dL$^1$), while blood concentrations for the experimental group seemed to peak at five hours post-ingestion (4.05±0.87 mg dL$^1$). However, it is quite possible that the peak for the experimental group may not have been fully achieved, and it is suggested that the blood concentrations may well be maintain in an elevated condition for the experimental group from a significant time past five hours post-ingestion, so that total integrated area under the curve for the experimental group is underreported herein. Nonetheless, the integrated area under the curve for the 5 hour period was 7-fold greater for the control group.

Both the control and experimental groups exhibited similar relative myosin heavy chain expression, indicating uptake was likely not influenced by fiber characteristics.

Although total creatine ingested over the supplementation period was less for the experimental group ingesting creatine HCl/PEG (50 g creatine equivalents total) as compared to the control group ingesting creatine.H$_2$O (100 g equivalents total), skeletal muscle uptake for creatine HCl/PEG and creatine.H$_2$O was similar.

Details of a study summarized above and now described are included in an Exhibit to U.S. Provisional Ser. No. 60/942,176 entitled THE EFFECTS OF TWO CREATINE FORMULATIONS ON MUSCLE AND SERUM CREATINE LEVELS, which is incorporated herein in its entirety by this reference. The control group of the study ingested 20 g/day of creatine equivalents in the form of creatine.H$_2$O in powdered form for 5 days. The experimental group of the study ingested 10 grams/day of creatine equivalents in the form of creatine HCl/PEG in tablet form for 5 days. Compliance with the supplementation protocol was 100% for all subjects completing the study. Two subjects were dismissed from the study due to an inability to place an indwelling canula in a superficial antecubital vein for the 5 hour post-supplementation blood sampling. Both of these subjects were in the experimental group. Additionally, the biopsy sample for one subject in the control group was lost during the centrifugation step of the extraction process. The net result was a sample size for the control group of n=9 and for the experimental group of n=8.

Each day, prior to the creatine ingestion, indwelling canulas with saline drips were inserted into a superficial antecubital vein of each participant. Circulating concentrations of creatine and other blood constituents and components measured from samples taken over a 5-hour period post-ingestion. Blood samples were obtained with in inline stopcock apparatus, thus allowing for multiple samples. These samples were immediately frozen and sent to a commercial clinical laboratory for analysis. FIG. 1 illustrates the timeline for blood sampling post-ingestion.

Pre and post muscle biopsies were obtained from the vastus lateralis muscle. Samples were immediately frozen in liquid nitrogen and stored at −80° C. for later analysis. The frozen samples were weighed to the nearest 0.1 mg, freeze dried for 8 hours and reweighed. The tissue samples were extracted and then analyzed for creatine, creatine phosphate, and ATP content via fluoroscopy.

The following dependent variables were used in the study:

Descriptive—age, height, body weight, relative fat.

Blood chemistries—glucose, uric acid, BUN, creatinine, BUN/creatinine, sodium, potassium, chloride, carbon dioxide, calcium, phosphorus, total protein, albumin, globulin, A/G ratio, bilirubin, alkaline phosphatase, LDH, AST (SGOT), ALT (SGPT), iron.

Blood CBC w/differential/platelet—WBC count, RBC count, hemoglobin, hematocrit, MCV, MCH, MCHC, RDW, platelets, neutrophils, lymphs, monocytes, eosinophils, basophils, neutrophils (absolute), lymphs (absolute), monocytes (absolute), eosinophils (absolute), basophils (absolute).

Urine analyses—pH, urine-color, appearance, WBC esterase, protein, glucose, ketones, occult blood, bilirubin, urobilinogen, semi-Qn, nitrite, microscopic examination.

Circulatory creatine uptake—blood creatine concentrations pre- and post-ingestion (pre, 15 min, 30 min, 1 hr, 2 hrs, 3 hrs, 4 hrs, 5 hrs).

Muscle creatine-related concentrations—Cellular concentrations of ATP, CP, free creatine (fCr), total creatine (tCr), CP/ATP, fCr/ATP, and tCr/Atp.

Dietary Records—Kcals, protein, carbohydrates, fats.

Figure 2:
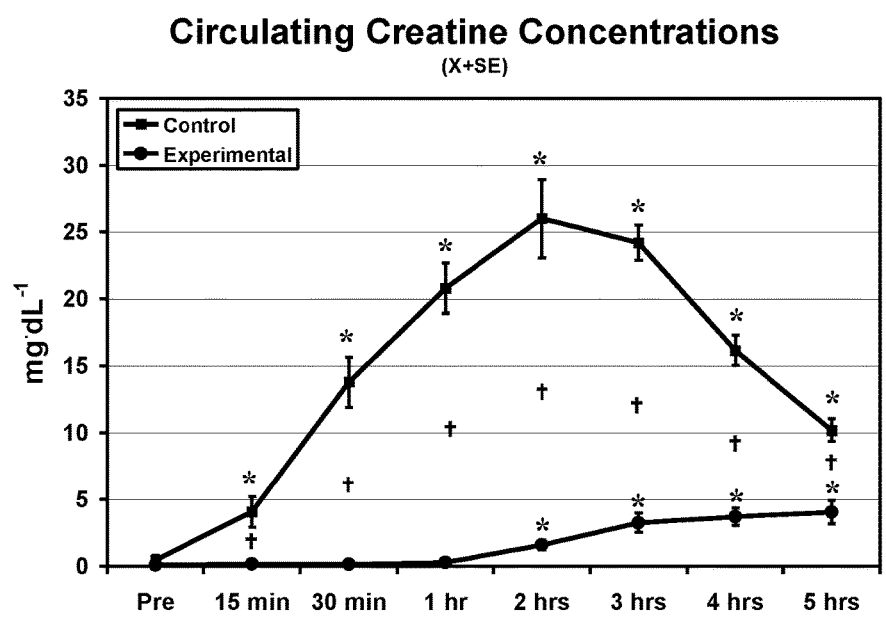
FIG. 2 illustrates levels of circulating creatine concentrations relating to the study referred to in FIG. 1 and described herein.

Table 2 below lists the blood concentrations of creatine post-ingestion. Concentrations for the control group increased significantly by 15 min, while the experimental group did not increase significantly until 2 hours. There was a significant difference between the groups at all times post-ingestion. The integrated area under the curve indicated that the control group had an approximately 7-fold greater blood concentration over the 5 hr sampling period. However, it appears that the 5 hour sampling period may not have been long enough since the values for the experimental group had not peaked, as is apparent from the lower tracing of FIG. 2.

TABLE 2

Circulating concentrations of creatine (mg · dL$^{-1}$ ± SE).

| Time | Control (n = 9) | Experimental (n = 8) |
|---|---|---|
| Pre | 0.47 ± 0.35 | 0.12 ± 0.03 |
| 15 min | 4.08 ± 1.14 | 0.19 ± 0.06 |
| 30 min | 13.79 ± 1.86 | 0.15 ± 0.05 |
| 1 hr | 20.81 ± 1.87 | 0.30 ± 0.10 |
| 2 hrs | 25.99 ± 2.96 | 1.59 ± 0.36 |
| 3 hrs | 24.20 ± 1.29 | 3.27 ± 0.70 |
| 4 hrs | 16.16 ± 1.13 | 3.72 ± 0.65 |
| 5 hrs | 10.21 ± 0.85 | 4.05 ± 0.87 |
| Integrated area under curve (mg · dL$^{-1}$ · 5 hrs$^{-1}$) | 91.8 ± 5.5 | 13.0 ± 7.1 |

Figure 3:
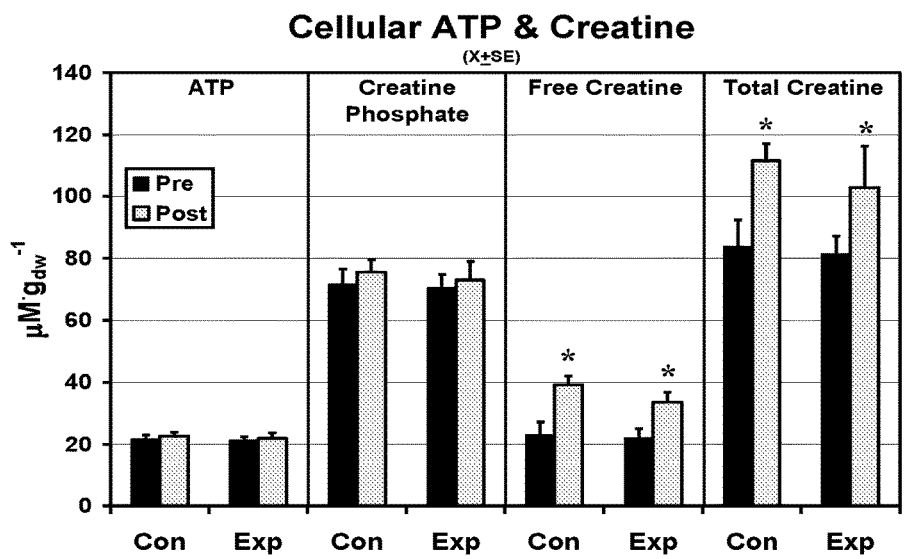
FIG. 3 illustrates levels of cellular ATP and creatine level relating to the study referred to in FIG. 1 and described herein.
Figure 4:
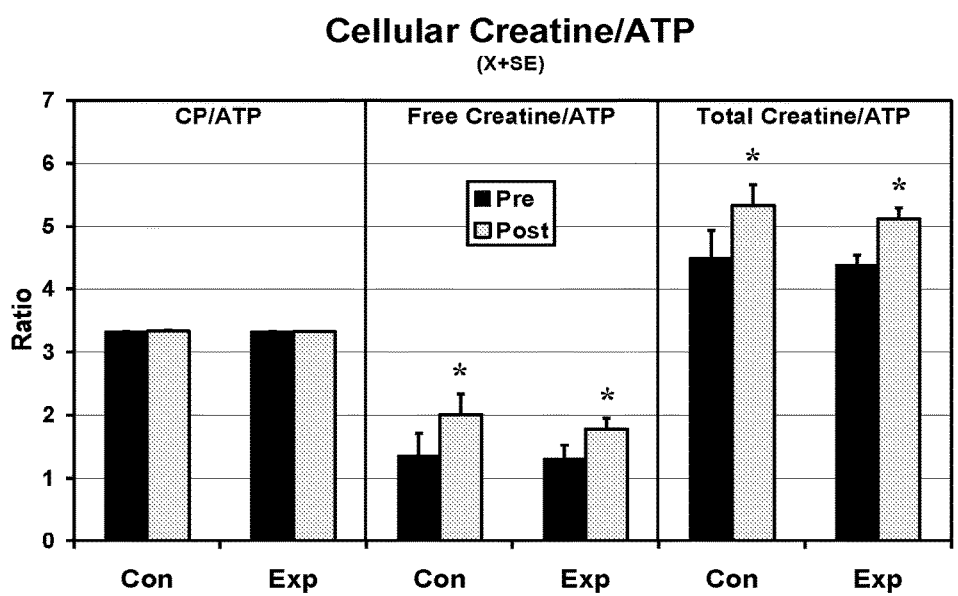
FIG. 4 illustrates ratios of creatine phosphate to ATP, free creatine to ATP, and total creatine to ATP relating to the study referred to in FIG. 1 and described herein.

Summary data listed in Table 3 below, and illustrated in FIGS. 3 and 4 show muscle concentrations of free creatine and total creatine. Both the control and experimental groups exhibited significant increases in free creatine and total creatine. The absolute values for total creatine represent increases of approximately 33% for the control group and 26% for the experimental group. These increases were still evident after adjusting these values for ATP concentrations. There were no differences exhibited between groups. Intra-assay reliabilities were CV=2.8% for the ATP and CP assay, and CV=1.2% for the creatine assay.

TABLE 3

ATP and creatine concentrations (X ± SE).

| | Control Group | | Experimental Group | |
|---|---|---|---|---|
| Variable | Pre | Post | Pre | Post |
| ATP (μM · g$_{dw}^{-1}$) | 21.6 ± 1.4 | 22.7 ± 1.2 | 21.2 ± 1.3 | 22.0 ± 1.8 |
| creatine phosphate (μM · g$_{dw}^{-1}$) | 71.7 ± 4.8 | 75.6 ± 4.0 | 70.5 ± 4.3 | 73.0 ± 6.0 |
| creatine phosphate/ATP$^{-1}$ | 3.33 ± 0.01 | 3.34 ± 0.01 | 3.33 ± 0.01 | 3.33 ± 0.01 |
| Creatine (μM · g$_{dw}^{-1}$) | 23.0 ± 4.2 | 39.2 ± 2.7 | 22.1 ± 2.9 | 33.6 ± 3.2 |
| Creatine · ATP$^{-1}$ (ratio) | 1.36 ± 0.36 | 2.01 ± 0.33 | 1.31 ± 0.22 | 1.78 ± 0.17 |
| Total creatine (μM · g$_{dw}^{-1}$) | 83.8 ± 8.5 | 111.6 ± 5.5 | 81.3 ± 5.8 | 102.8 ± 13.5 |
| Total creatine · ATP$^{-1}$ (ratio) | 4.49 ± 0.45 | 5.33 ± 0.33 | 4.39 ± 0.15 | 5.13 ± 0.18 |

Table 4 lists the results for the blood chemistry tests associated with the study.

TABLE 4

Blood chemistries (±SE)

| Variable | Time | Control Group | Experimental Group |
|---|---|---|---|
| Creatinine, Serum (mg · dL$^{-1}$) | Pre | 0.93 ± 0.04 | 1.01 ± 0.05 |
| | Post | 1.09 ± 0.07 | 1.49 ± 0.08† |
| Glucose, Serum (mg · dL$^{-1}$) | Pre | 86.7 ± 2.7 | 92.8 ± 2.9 |
| | Post | 82.6 ± 4.3 | 85.5 ± 4.6 |
| Uric Acid, Serum (mg · dL$^{-1}$) | Pre | 5.6 ± 0.3 | 5.9 ± 0.3 |
| | Post | 4.7 ± 0.2 | 5.3 ± 0.3 |
| BUN (mg · dL$^{-1}$) | Pre | 16.4 ± 1.4 | 15.0 ± 1.5 |
| | Post | 17.9 ± 1.8 | 13.9 ± 1.9 |
| BUN/Creatinine (ratio) | Pre | 17.8 ± 1.3 | 14.6 ± 1.4 |
| | Post | 16.3 ± 1.4 | 9.5 ± 1.4† |
| Sodium, Serum (mM · L$^{-1}$) | Pre | 139.1 ± 0.5 | 139.8 ± 0.5 |
| | Post | 138.6 ± 0.6 | 138.6 ± 0.7 |
| Potassium, Serum (mM · L$^{-1}$) | Pre | 4.3 ± 0.1 | 4.3 ± 0.1 |
| | Post | 4.4 ± 0.1 | 4.3 ± 0.1 |
| Carbon Dioxide (mM · L$^{-1}$) | Pre | 26.7 ± 0.4 | 27.5 ± 0.4 |
| | Post | 25.8 ± 0.7 | 24.1 ± 0.8 |
| Calcium, Serum (mg · dL$^{-1}$) | Pre | 9.9 ± 0.1 | 9.9 ± 0.1 |
| | Post | 9.7 ± 0.1 | 9.9 ± 0.1 |
| Phosphorus, Serum (mg · dL$^{-1}$) | Pre | 4.3 ± 0.1 | 4.3 ± 0.1 |
| | Post | 4.3 ± 0.3 | 4.0 ± 0.3 |

TABLE 4-continued

Blood chemistries (±SE)

| Variable | Time | Control Group | Experimental Group |
|---|---|---|---|
| Protein, Serum (g · dL$^{-1}$) | Pre | 7.1 ± 0.1 | 7.1 ± 0.2 |
| | Post | 6.9 ± 0.1 | 7.1 ± 0.1 |
| Chloride, Serum (mM · L$^{-1}$) | Pre | 101.0 ± 0.5 | 101.3 ± 0.5 |
| | Post | 101.9 ± 0.7 | 103.4 ± 0.7 |
| Albumin, Serum (g · dL$^{-1}$) | Pre | 4.5 ± 0.1 | 4.5 ± 0.1 |
| | Post | 4.5 ± 0.1 | 4.5 ± 0.1 |
| Globulin, Serum (g · dL$^{-1}$) | Pre | 2.6 ± 0.1 | 2.6 ± 0.1 |
| | Post | 2.4 ± 0.1 | 2.5 ± 0.1 |
| A/G Ratio (ratio) | Pre | 1.77 ± 0.06 | 1.75 ± 0.07 |
| | Post | 1.88 ± 0.06 | 1.80 ± 0.06 |
| Bilirubin, Total (mg · dL$^{-1}$) | Pre | 0.6 ± 0.1 | 0.7 ± 0.1 |
| | Post | 0.6 ± 0.1 | 0.6 ± 0.1 |
| Alk. Phosphatase (IU · L$^{-1}$) | Pre | 78.7 ± 10.1 | 89.0 ± 10.7 |
| | Post | 85.4 ± 9.3 | 92.8 ± 9.9 |
| LDH (IU · L$^{-1}$) | Pre | 155.0 ± 6.0 | 152.5 ± 6.4 |
| | Post | 157.9 ± 8.2 | 148.4 ± 8.7 |
| AST (SGOT) (IU · L$^{-1}$) | Pre | 25.3 ± 3.6 | 27.3 ± 3.8 |
| | Post | 23.3 ± 2.1 | 24.9 ± 2.2 |
| ALT (SGPT) | Pre | 24.1 ± 4.5 | 28.0 ± 4.8 |
| | Post | 20.9 ± 4.1 | 27.8 ± 4.4 |
| Iron, Serum (μg · dL$^{-1}$) | Pre | 88.8 ± 10.5 | 100.1 ± 11.1 |
| | Post | 103.3 ± 14.2 | 86.4 ± 15.0 |

Figure 5:
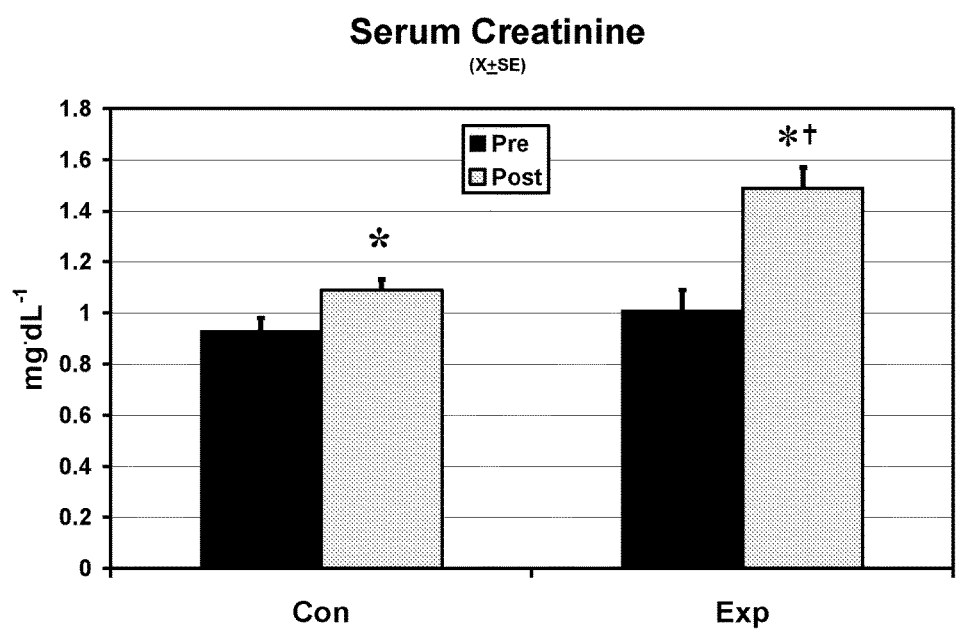
FIG. 5 illustrates levels of serum creatinine relating to the study referred to in FIG. 1 and described herein.

FIG. 5 illustrates the serum creatinine concentrations which indicate a difference between groups. These differences, however, are still within normal ranges for healthy individuals, although the mean post values for the experimental group are at the high end of the range.

Perhaps the most critical data generated concern creatine uptake by the muscle. Both the control and experimental groups exhibited similar ATP, creatine phosphate, free creatine and total creatine at the beginning of the study. Both groups also exhibited similar increases in free creatine and total creatine during the post-test despite the different dosages. This indicates an enhanced uptake of the creatine for the experimental group. In the event that biopsy samples may have included excessive blood or connective tissue that would have confounded the results, creatine levels were adjusted for ATP levels, although this adjustment still resulted in elevations of free and total creatine. It appears that in the present study, the biopsy samples were relatively similar in that they did not contain excessive amounts of blood or connective tissue. The creatine values observed in the present study are similar to values previously reported in the creatine scientific literature, although total creatine concentrations post-supplementation were slightly less for both groups than has been previously reported.

It should be noted that although all serum creatinine levels were within normal ranges, there was a significant difference between groups by the post-test. While this may simply be due to the normal fluctuations for this variable, it is also possible that the enhanced cellular uptake evident for the experimental group permitted more creatine to be taken up by the cell and ultimately degraded to creatinine.

On a practical note, the size of the tablets used for the experimental group may be problematic for some individuals, although all our subjects subjectively reported no problem in swallowing the tablets. However, the quantity of tablets (16) needed to ingest the 10 g dose may be considered large by some. If there is indeed an inability for some of the tablets to completely dissolve in the GI tract, it could contribute to a lower uptake of creatine into the blood. It should be noted, however, that this was reported by only one subject and could not be verified by any of the investigative team.

In summary, the data from the present study indicates that association of polyethylene-glycol (PEG) with the creatine molecule permits creatine it to be more effectively taken up by the muscle cell, despite considerably lower circulating creatine concentrations in the blood during the 5 hours post-ingestion. While not fully understanding the mechanism of action of the present invention after ingestion, based on circulating creatine concentrations measured, it appears that the creatine polyethylene glycol ingested by the experimental group clears more slowly from the gastrointestinal tract, and thus is made available to the individual over a more extended period of time, possibly contributing to enhanced muscle uptake. Accordingly, it is postulated that the lower dosages of creatine may be ingested using the compositions of the present invention, while maintaining optimal loading kinetics.

The enteric-coated, PEG and soluble creatine blends of the present invention, and in particular the most preferred embodiment which comprises an enteric-coated dispersion of creatine HCl dispersed in PEG is expected to be useful for minimizing symptoms of Parkinson's disease and of muscle-wasting diseases. Preferred dosages are expected to be in the range of 0.1 to 10 grams per day of creatine equivalent. However, it is also contemplated that once creatine loading has occurred, lower dosages may be preferred, at from 0.5 to 2 grams, per day of creatine equivalent. Even lower dosages of from 0.01 to 0.5 grams per day of creatine equivalent are expected to have beneficial results, and may have particular utility when taken by, the elderly. Conversely, dosages of 10-20 grams per day of creatine equivalent are expected to have important therapeutic effect.

In alternate embodiments, liquid formulations in a liquid PEG such as having average molecular weights of from 190 to 210 (e.g., Carbowax® PEG 200), from 285 to 315 (e.g., Carbowax® PEG 300), from 380 to 420 (e.g., Carbowax® PEG 400) and from 570-63 (e.g., Carbowax® PEG 600) may be used.

Also, in addition to the enteric-coated pill form of the creatine formulations of the present invention, other conventional enteric-coatings are contemplated, as are other forms, such as caplets and other dosing formulations.

The creatine formulations and other embodiments of the present invention are expected to have particular utility for minimizing symptoms of Parkinson's disease and of muscle-wasting diseases and conditions, including but not limited to polymyositis, cachexia due to metabolic disease, cachexia due to cancer, anorexia nervosa, myasthenia gravis and rhabdomyolysis. When the creatine formulations and other embodiments of the present invention are used it minimize symptoms of Parkinson's disease and of muscle-wasting diseases and conditions, a regimen of from 2 to 20 grams per day of the creatine equivalent is contemplated.

The invention claimed is:

1. An oral creatine formulation comprising:
   a solid dispersion of
      creatine hydrochloride; and
      solid polyethylene glycol having an average molecular weight of from 3015 to 4800,
   wherein the creatine hydrochloride ("creatine.HCl") and polyethylene glycol ("PEG") are present in a weight ratio of from 95:5 to 90:10 of creatine.HCl:PEG and are coated with an enteric coating, and a dosage of the formulation is from 0.1 to 10 grams per day of creatine from the creatine HCl.

2. The creatine formulation of claim 1, wherein the polyethylene glycol has an average molecular weight of from 3015 to 3685.

3. The creatine formulation of claim 1, wherein the polyethylene glycol has an average molecular weight of from 3600 to 4400.

4. The creatine formulation of claim 1, wherein the polyethylene glycol has an average molecular weight of from 4400 to 4800.

5. An oral creatine formulation consisting essentially of:
   a solid dispersion of
      creatine hydrochloride; and
      polyethylene glycol having an average molecular weight of from 3015 to 4800,
   wherein the creatine hydrochloride ("creatine.HCl") and polyethylene glycol ("PEG") are present in a weight ratio of from 95:5 to 90:10 of creatine.HCl:PEG and are coated with an enteric coating, and a dosage of the formulation is from 0.1 to 10 grams per day of creatine from the creatine HCl.

6. The creatine formulation of claim 5, wherein the polyethylene glycol has an average molecular weight of from 3015 to 3685.

7. The creatine formulation of claim 5, wherein the polyethylene glycol has an average molecular weight of from 3600 to 4400.

8. The creatine formulation of claim 5, wherein the polyethylene glycol has an average molecular weight of from 4400 to 4800.

* * * * *